Figure 1A:
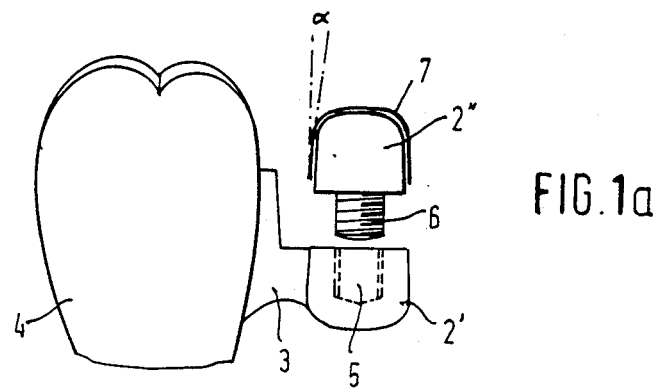

United States Patent [19]

Weber

[11] Patent Number: 4,880,383

[45] Date of Patent: Nov. 14, 1989

[54] MAGNETIC FASTENING SYSTEM FOR DENTAL PROSTHESIS

[75] Inventor: René Weber, Schmitten, Switzerland

[73] Assignee: I.D.R. B.V., Boerhaaveplein, Netherlands

[21] Appl. No.: 123,606

[22] Filed: Nov. 20, 1987

[51] Int. Cl.[4] ............................................. A61C 13/235
[52] U.S. Cl. .................................... 433/189; 433/180; 433/181
[58] Field of Search ......................... 433/189, 180, 181

[56] References Cited

U.S. PATENT DOCUMENTS

| | | | |
|---|---|---|---|
| 1,394,770 | 10/1921 | Yirikian | 433/181 |
| 1,841,870 | 1/1932 | Yirikian | 433/180 |
| 2,732,621 | 1/1956 | Pelzmann | 433/189 |
| 4,184,252 | 1/1980 | Krol et al. | 433/189 |
| 4,209,905 | 7/1980 | Gillings | 433/189 |
| 4,214,366 | 7/1980 | Laban | 433/189 |
| 4,242,089 | 12/1980 | Sasaki | 433/189 |
| 4,247,286 | 1/1981 | Herrera et al. | 433/170 |
| 4,302,189 | 11/1981 | Gillings | 433/189 |
| 4,626,213 | 12/1986 | Shiner et al. | 433/189 |
| 4,693,686 | 9/1987 | Sendax | 433/189 |

FOREIGN PATENT DOCUMENTS

| | | | |
|---|---|---|---|
| 3140464 | 4/1983 | Fed. Rep. of Germany | 433/189 |
| 2583633 | 12/1986 | France | 433/189 |
| 2587895 | 4/1987 | France | 433/189 |

Primary Examiner—John J. Wilson
Attorney, Agent, or Firm—Gottlieb, Rackman & Reisman

[57] ABSTRACT

A system for fastening a dental prosthesis comprising a support element to be fitted in the mouth and a fastening element to be fitted on the prosthesis with the support element being designed to detachably retain said fastening element. According to the invention, the support element comprises a bottom portion and a top portion. At least the top portion is made, at least in part, of magnetic material, and the support element has an essentially oval contour in sideview and includes attaching means for attaching it to at least one dental element. The fastening element comprises a cover plate of magnetically receptive material capable of at least partially embracing the support element.

11 Claims, 1 Drawing Sheet

MAGNETIC FASTENING SYSTEM FOR DENTAL PROSTHESIS

This invention relates to a system for fastening a dental prosthesis comprising a support element to be fitted in the mouth and a fastening element to be fitted on the prosthesis with the support element being designed to detachably retain said fastening element.

There is already a fastening system for dental prostheses which is known by the name of extracoronary fastening system. In it, dental prostheses can be detachably fastened to support elements which, in their turn, can be fitted on, or in, dental elements still present in the upper or lower jaw. The detachable attachment of the prosthesis in the mouth is accomplished, in that system, by means of a press button construction, in which the support element carries one part of the press button and the fastening element carries the other part of the press button. Similar screw and slide constructions are also known.

The disadvantage of this manner of retention is not only that a great many different components are required, but in particular that the press button part permanently fitted in the mouth, which commonly is an annular element which is open at the top and bottom, is prone to contamination and is not easily cleaned. Moreover, the gums tend to grow into the annular space, which makes cleaning still more difficult and in addition may give rise to irritation.

It is an object of the present invention to provide a system which does not have the disadvantages outlined above. For this purpose, the invention provides a system of the above kind in which the support element comprises a bottom portion and a top portion with at least the top portion being made, at least in part, of magnetic material, said support element having an essentially oval contour in sideview and including attaching means for attaching it to at least one dental element, the fastening element comprising a cover plate of magnetically receptive material capable of at least partially embracing said support element.

The advantage of the system according to the invention is that it is simple of construction, comprises few separate components, and in particular that it is very easy to clean by virtue of the complete absence of apertures, slots and the like in the support element permanently present in the mouth.

The oval shape of the support element and the adapted shape of the cover plate offer the possibility for these elements to move relatively to each other, so that the prosthesis may hinge relatively to the existing dental elements and, for example, during chewing, no undue forces are exerted on the prosthesis. On the other hand, it is possible for the prosthesis to be rigidly attached to the crowns fitted on existing dental elements, which may be desirable, for example, when a prosthesis is attached between two crowns. For such a rigid attachment, the cover plate and the support element may be complementary in shape so as to exclude relative movement.

In order to make for some resilience in a direction perpendicular to the jaw, which makes chewing more comfortable, a layer of resilient material suitable for dental purposes may be provided between the cap-shaped cover plate and the support element or between the cover plate and the actual prosthesis.

It is observed that FR-A-2076270 discloses a fastening system for dental prostheses, using magnetic force. In it, a root cap with a frustoconical support element of a magnetic material is fitted in the jaw as a support element, and the prosthesis is provided with a cap-shaped support element of magnetic or magnetisable material cooperating therewith. The disadvantage of that system is that it is expensive. In the system according to the present invention, the support element is fastened to a crown on a dental element that is still present, which makes for a less expensive treatment.

Figure 2:
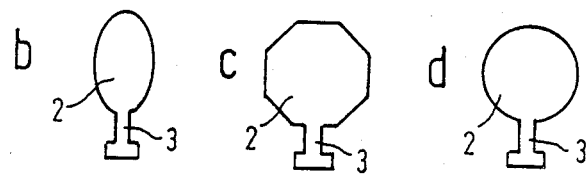
Figure 2:
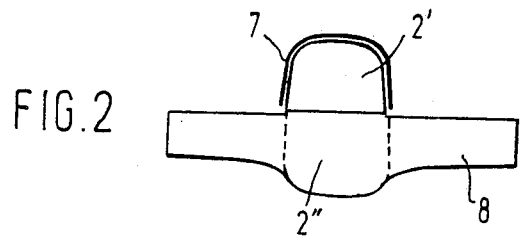

Some embodiments of the invention will now be described, by way of example, with reference to the accompanying drawings, in which:

FIG. 1a shows a side-elevational view of the system according to the invention;

FIGS. 1b, c, d show different contours in top plan view of the support element of the system shown in FIG. 1; and FIG. 2 shows a side-elevational view of a second embodiment according to the invention.

FIG. 1 shows a side-elevational view of the system according to the present invention with a support element 2 which in the embodiment shown consists of a bottom portion 2′ and a top portion 2″. The bottom portion 2′ is secured by means of a support 3 to a dental element or to a crown 4 fitted on a dental element still present in the mouth. The bottom portion 2′ and support 3 consist, for example, of metal, with the portions 2′ and 3 being possibly cast with the crown 4 or possibly secured to it later by soldering or in any other known manner. Portions 2′ and 3 may alternatively consist of synthetic plastics and be secured to the crown in known manner.

Formed in the bottom portion 2′ of support element 2 is a threaded hole 5. In the case of a metal bottom portion 2′, the screw thread is formed in the metal itself, while in a plastics bottom portion 2′ a metallic threaded bushing is mounted in the plastics.

The top portion 2″ of the support element 2 consists at least in part of a magnetic material and is provided with a threaded projection 6 which can be screwed in a hole 5. Various suitable magnetic materials are known in the art of dentistry for the material of the upper portion 2″. If desired, the magnetic material may be provided with a coating to prevent corrosion.

Instead of a support element composed of two loose elements 2′ and 2″, this may, if desired, be formed as one whole, in which case the threaded projection 6 and hole 5 can be done without.

When, in the embodiment shown, the top portion 2″ has been screwed to the bottom portion 2′, the support element has an oval shape in sideview, in any case with no flat surface at the bottom side. The angle α between the longitudinal axis of support element 2 and the side face thereof may, for example, be about 6°. The essentially oval shape of the support element has the advantage that it can be very easily cleaned and that, specifically, the space under the underside of the bottom portion 2′ can easily be cleaned owing to the absence of a flat face, while no debris can collect as a result of capillary action between this underside and the juxtaposed gums, which risk does exist if the underside of the bottom portion 2′ were flat.

FIGS. 1b, c and d show a number of different top plan views of the support element 2, namely, a round shape, a heptagonal shape and an oval shape. However, various other shapes are possible.

The fastening element to be placed on the support element 2 comprises a cap-shaped cover plate 7. In the figure, this cover plate 7 is shown only, because the prosthesis itself and the manner in which the cover plate is secured to the prosthesis are immaterial for a good understanding of the invention and, in addition, will be clear to those skilled in the art.

Cover plate 7 is made of magnetically receptive material, for example, a ferromagnetic material, so that the prosthesis can be retained by means of the cover plate to the support element by magnetic force. The cover plate preferably embraces the entire support element portion 2″ to profit optimally from the magnetic force. Cover plate 7 has such a shape that it closely fits on the support element to ensure optimum attraction by the magnet, for example, a shape complementary to that of support element 2, i.e. for example, a round, heptagonal or oval shape with a support element shaped as shown in the respective FIGS. 1b, 1c and 1d.

In the case of a round or oval support element with a complementarily shaped cover plate, the cover plate, and hence, the prosthesis, may tilt somewhat relatively to the support element. In the case of a heptagonal or otherwise angled support element, such a movement is hardly, if at all, possible. This may be desirable if the prosthesis is carried on opposite sides by support elements, such as element 2, secured to crowns.

FIG. 2 shows the system according to the invention as a part of a different type of extracoronary fastening element. The support element 2 forms part of a rod 8 secured on opposite ends, for example by means of soldering, to crowns fitted on dental elements still present in the mouth.

It will be clear that many variants are possible within the scope of the present invention, depending on the use of the various known dental materials and the specific type of prosthesis to be fastened. Thus, the support element 2 may alternatively be carried by means of arm 3 by a plurality of crowns located in one row, while arm 3 may be absent, in which case the portion 2′ of the support element forms part of the crown proper.

I claim:

1. A dental prosthesis system for use in a mouth of a patient comprising:
   a support element retained in the patient's mouth, said support element comprising a top portion and a bottom portion, said top portion and said bottom portion each having a substantially curved surface, said top portion comprised at least in part of a magnetic material;
   means for attaching said support element to a side face of at least one dental element already present in the patient's mouth; said attaching means being connected to said bottom portion and comprising a support arm on at least one side of said bottom portion;
   a fastening element secured to a prosthesis, said fastening element comprising a cover plate of magnetically receptive material having a shape suitable for partially embracing the top portion of said support element; and
   wherein said support element is detachably connected to said fastening element by magnetic forces when the top portion is encased in said fastening element.

2. The dental prosthesis system of claim 1, wherein said top portion of said support element is detachably and pivotally connected to said fastening element.

3. The system of claim 2, wherein the top portion of said support element is detachably connected to the bottom portion of said support element.

4. The system of claim 3, wherein said top portion is detachably connected to said bottom portion by means of a screw connection.

5. The system of claim 1, wherein said attaching means comprises support arms disposed on opposite sides of said bottom portion of said support element.

6. The system of claim 1, wherein the bottom portion of the support element is made of metal.

7. The system of claim 1, wherein the bottom portion of the support element is made of synthetic plastic material.

8. The system of claim 1, wherein the support element has a substantially round circumferential configuration.

9. The system of claim 1, wherein the support element has a substantially oval configuration.

10. The system of claim 1, wherein the support element has a substantially polygonal configuration.

11. The system of claim 1, wherein the cover plate of said fastening element is covered on one side thereof with a layer of resilient material.

* * * * *